US006783584B2

(12) United States Patent
Takahashi

(10) Patent No.: US 6,783,584 B2
(45) Date of Patent: Aug. 31, 2004

(54) HIGH-CHROMATIC FLAKY PIGMENT COATED WITH SEMI-TRANSPARENT FILM

(75) Inventor: Norio Takahashi, Fukushima Pref (JP)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/245,292

(22) Filed: Sep. 18, 2002

(65) Prior Publication Data

US 2003/0051634 A1 Mar. 20, 2003

(30) Foreign Application Priority Data

Sep. 18, 2001 (JP) ....................................... 2001-282600

(51) Int. Cl.[7] .................................................. C09C 1/62

(52) U.S. Cl. ....................... 106/403; 106/404; 106/415; 106/418; 106/419; 106/425; 106/435; 106/436; 106/438; 106/439; 106/447; 106/454

(58) Field of Search ................................ 106/403–404, 106/415, 418–419, 425, 435–436, 438, 439–447, 454

(56) References Cited

U.S. PATENT DOCUMENTS

| | | | | | |
|---|---|---|---|---|---|
| 2,885,366 | A | * | 5/1959 | Iler | 516/90 |
| 5,352,286 | A | * | 10/1994 | Schmid et al. | 106/404 |
| 5,364,467 | A | * | 11/1994 | Schmid et al. | 106/404 |
| 5,607,504 | A | * | 3/1997 | Schmid et al. | 106/403 |
| 5,733,364 | A | * | 3/1998 | Schmid et al. | 106/403 |
| 2003/0005859 | A1 | * | 1/2003 | Andes et al. | 106/403 |

* cited by examiner

*Primary Examiner*—C. Melissa Koslow
*Assistant Examiner*—Shalie Manlove
(74) *Attorney, Agent, or Firm*—Millen, White, Zelano, Branigan, P.C.

(57) ABSTRACT

To provide a high-chromatic flaky pigment with good colorability, and to provide a method for producing the flaky pigment in a simple and inexpensive plant. A high-chromatic flaky pigment of which the entire surface of the flaky substrate coated with a metal oxide having an interference color is further coated with a semi-transparent thin metal film to enhance the interference color of the pigment.

20 Claims, No Drawings

HIGH-CHROMATIC FLAKY PIGMENT COATED WITH SEMI-TRANSPARENT FILM

BACKGROUND OF THE INVENTION

Decorative pigments are used in various fields of cosmetics, plastics, paints, etc. Their typical examples are pearlescent pigments, metallic pigments, thin metal film-deposited film chips, etc.

Pearlescent pigments are widely used as coloring matters of pearly gloss, but when compared with metallic pigments, they are problematic in point of their luster (brilliance) and their hiding power (hiding ability of back ground) ability.

Metallic pigments are widely used, for example, typically for paints. In particular, aluminum flakes are one typical example of silver metallic pigments and are highly brilliant. They are inexpensive, and are stably supplied on the market. Recent attempts in the art of pigments with hiding power such as aluminum flakes, are to attain new colors. Metallic pigments have a strong metallic luster and their hiding power is good. But, when compared with pearlescent pigments, their appearance is often poor as their reflection light is too strong. In particular, conventional metallic pigments coated with metal oxides having high refractive index or the like to provide an interference color are problematic in that their color is weak.

Film chips having a vapor-deposited thin film of metal, have a metallic luster, are lightweight, and are easy to handle. However, they require a step of cutting the films in their production. For example, an optically variable pigment(a pigment having different hue when viewed from different angles) is prepared by deposition of aluminum or the like, a dielectric layer and further a metal film as semi-transparent reflecting layer, and this has a flop effect appearance and high chromaticity. However, since this is prepared by depositing a thin metal layer with sputtering equipment, it cannot be directly coated into fine particles like ordinary pigments. In practice, this requires a step of cutting the metal film-deposited sheet into pigment chips. Therefore, the edges of the thus-cut pigment chips are not coated with the metal film, and their waterproofness and heat resistance are not good. This is especially problematic when the substrate is a metallic pigment. In addition, the sputtering equipment is generally large and expensive. Apart from the above, also disclosed is a technique of coating the surface of aluminum flakes or the like with a multi-layered film through chemical vapor deposition methods. However, this is still not sufficient for forming a uniform submicron-order film on flaky substrates. In addition, this requires large-scale expensive equipment like the sputtering equipment as above (See Japanese Patent Laid-Open No. 258579/1995).

SUMMARY OF THE INVENTION

The subject matter of the invention includes solving the problems discussed above, and providing a high-chromatic flaky pigment having enhanced interference colors and di-chromatic effect, and also providing a method for producing the flaky pigment in a simple and inexpensive apparatus.

On this basis, the present inventors have discovered a flaky pigment having high-chromatic interference color. Particularly, it was found that coating a metal oxide-coated flaky pigment further with a semi-transparent thin metal film, provides a pigment with a strong interference color and flop effect.

In one embodiment the invention includes a high-chromatic flaky pigment, the entire surface of the flaky substrate being coated with a metal oxide providing an interference color and further coated with a semi-transparent thin metal film to enhance the interference color of the pigment.

The invention also relates to the high-chromatic flaky pigment in which the flaky substrate is preferably a metal pigment.

The invention further relates to the high-chromatic flaky pigment in which the metal oxide having an interference color is preferably one or more metal oxides selected from the group consisting of titanium dioxide, zirconium oxide, iron oxide, zinc oxide, tin oxide and cerium oxide.

The invention further relates to the high-chromatic flaky pigment in which the semi-transparent thin metal film preferably has a thickness of at most 0.05 $\mu$m.

The invention further relates to the high-chromatic flaky pigment in which the semi-transparent thin metal film is preferably formed of one or more metals selected from a group consisting of Ni, Zn, Cr, Co, Cu, Pt, Ag, Au, and their alloys.

The invention further relates to the high-chromatic flaky pigment in which the semi-transparent thin metal film is preferably a dense film of metal particles aligned continuously therein.

The invention further relates to the high-chromatic flaky pigment in which the semi-transparent thin metal film is preferably formed through reduction of an acetylacetonato-metal complex in an organic solvent.

The invention further relates to the high-chromatic flaky pigment in which the flaky substrate is preferably a metal pigment coated with a silicon dioxide film or an aluminum oxide as a protective film.

The invention further relates to the high-chromatic flaky pigment in which the flaky substrate preferably is of aluminum flakes.

The invention further relates to a method for producing a high-chromatic flaky pigment, which comprises coating the entire surface of a flaky substrate with a metal oxide, further coating the entire surface of the metal oxide-coated flaky pigment with a metal layer through reduction of an acetylacetonato-metal complex in an organic solvent, and drying it to form a semi-transparent thin metal film thereon.

The invention further relates to the use of the flaky pigment for paints, inks, security inks, powder coatings, plastics, resin moldings, cosmetics, for the preparation of granules, or for preventing forgeries by use in a security document.

The high-chromatic flaky pigment of the invention is preferably coated with a metal oxide which has high refractive index. Therefore, the metal oxide-coated flaky pigment has an interference color of itself, and its color reproducibility is good in its production.

According to the invention, a flaky pigment coated with a metal oxide having an interference color is further coated with a semi-transparent thin metal film, and, surprisingly, its interference color is thereby enhanced directly as it is, and, in addition, the thus-coated flaky pigment has di-chromatic effect.

Moreover, since the flaky pigment of the invention is characterized in that the entire surface of its substrate is coated with a thin metal oxide film and further with a semi-transparent thin metal film, it has excellent waterproofness, durability and heat resistance. The semitransparent thin metal film is also provided over the entire surface of the metal oxide film.

Further, according to the invention, a uniform and dense thin film of metal particles can be formed to cover the surface of a flaky pigment in an extremely simple and inexpensive method not requiring an expensive large-scale apparatus such as a sputtering unit.

The invention is described in more detail hereinunder, but is not limited to the following description.

Flaky Substrate

The flaky substrate, that is, the pigment substrate for use in the invention may be a metal pigment in flake form, including, for example, aluminum, stainless steel, titanium, copper, brass, tin, iron, bronze, cuprite, etc. For example, aluminum flakes are preferred, as they are commercially stably supplied and are inexpensive. Preferably, the pigment particles have a average size falling between 5 and 100 μm, more preferably between 5 and 50 μm. Such pigment particles not larger than 100 μm in size are preferred, as they well disperse in coating compositions, not sedimenting therein, and are easy to handle. They may have a thickness falling between 0.1 and 5 μm.

Protective Film

Of the flaky substrates, it is desirable that the metal pigment is previously coated with a protective film. With the coating, the stability and the weather resistance of the metal pigment itself are improved, and, in addition, the adhesiveness between the metal pigment and a metal oxide layer to be formed to cover it is improved. In particular, aluminum flakes, when used as the metal pigment substrate, will generate hydrogen gas as a result of reaction with water in a metal oxide coating process. Therefore, they are preferably previously coated with a protective film so as to prevent their surface activity. In principle, it is desirable that the protective film is colorless and has a low refractive index. For example, silica, alumina or the like may be used for the protective film. For coating the pigment substrate with such a protective film, any known method can be used.

Regarding its amount, the protective film must not have any influence on the optical properties of the metal pigment substrate coated with it. For example, the amount of the protective film may fall between 0.1 and 10% by weight of the flaky substrate coated with it, preferably between 1 and 5% by weight.

For coating the flaky substrate with such a protective film, for example, preferred is a sol-gel method. The sol-gel method comprises forming a sol through hydrolysis and poly-condensation of a solution of an organic metal compound or the like, followed by gelling it. Next, the resulting gel is heated to form a metal oxide. In this invention, one preferred example of the organic metal compound capable of being subjected to hydrolysis and polycondensation is an alkoxyl group-containing metal alkoxide. Particularly, it includes silicon methoxides, ethoxides, propoxides, etc., such as tetrametho-xysilane, tetraethoxysilane, tetraisopropoxysilane, methyl-triethoxysilane, dimethyl-dimethoxysilane, etc. The metal alkoxide also includes aluminum methoxides, ethoxides, propoxides, etc., for example, trimethoxyaluminate, triethoxyaluminate, tripropoxy-aluminate, etc.

In addition, bi-component silica-alumina is also usable for the protective film, and it may be formed from cohydrolysis-polycondensation of a combined system of an alkoxysilane and an alkoxyaluminum.

The solvent for dissolving metal alkoxides includes, for example, methanol, ethanol, propanol, butanol, pentanol, etc. Water is added to the solution of such an organic metal compound to hydrolyze and polycondense it.

Metal Oxide Film

The surface of the flaky substrate is coated with a metal oxide having high refractive index. The thus-coated flaky substrate provides an interference color, depending on the amount (optical thickness (refractive index×geometric thickness) of the metal oxide formed to coat the substrate. Distinctive portions of the light are reflected at two phase boundaries, i.e., between the inner surface of the metal oxide and the surface of flaky substrate. The interference of the individual portions of the light intensity occurs for different wavelengths and phase difference. These intensity differences are perceived by the eye as color, which varies from gold to green, depending on the amount of the metal oxide layer.

The intensity of the interference color is higher when the difference of refractive index between the two media is larger, and, in addition, the geometric thickness of the interference color layer can be reduced more. Therefore, it is advantageous that the metal oxide used to cover the flaky substrate have a higher refractive index. For example, the metal oxide is preferably titanium dioxide, zirconium oxide, iron oxide, tin oxide or cerium oxide. Especially preferred is titanium dioxide.

The metal oxides having high refractive index are preferred, as the thickness of their films can be controlled by visual observation in their formation, and their color reproducibility is good.

Regarding its amount, it is desirable that the metal oxide film is formed to cover the flaky pigment substrate to such a amount that the thickness presents the intended interference color.

For example, for presenting the intended interference color, the optical thickness of the metal oxide film preferably falls between 90 and 210 nm for gold; between 210 and 250 nm for red; between 250 and 310 nm for blue; and between 310 and 360 nm for green.

For coating the pigment substrate with such a metal oxide film, employable is any known method. Various coating methods such as thermal deposition and neutralization hydrolysis, for example, in aqueous coatings from titanium sulfate, titanium chloride, and sol-gel method are well known.

All these coating methods do not include a step of cutting pigments, and therefore, the flaky substrate is entirely coated with the metal oxide film layer even over the edges of the flaky substrates.

In the present invention, the sol-gel method is especially preferred. This is because, if the protective film-coated aluminum flakes are processed in other aqueous coating methods of using titanium chloride, etc., the protective film will be cracked and water having penetrated through the cracks will react with aluminum to form hydrogen. The sol-gel method is free from this problem.

The sol-gel method for forming the metal oxide film may be the same as that for forming the protective film mentioned above. For example, when a titanium dioxide film is formed, the organic metal compound to be used may be titanium tetraalkoxides such as titanium tetramethoxide, titanium tetraethoxide, titanium tetrabutoxide, etc.

For forming a zirconium oxide film, usable are zirconium tetraalkoxides such as zirconium tetraethoxide, zirconium tetrapropoxide, zirconium tetrabutoxide, etc.

For forming a cerium oxide film, usable are cerium tetraalkoxides such as cerium tetramethoxide, cerium tetrapropoxide, etc.

For forming a tin oxide film, usable are tin octylate, dibutyl-tin dilaurate, dioctyl-tin oxide, etc. The solvent for dissolving the metal alkoxides and the method for dissolving them in the solvent may be the same as those for the sol-gel method for forming the protective film as above.

Semi-transparent Thin Metal Film

The semi-transparent thin metal film to cover the metal oxide-coated flaky pigment substrate is described below.

The metal to form the film includes, for example, Ni, Zn, Cr, Co, Cu, Pt, Ag, Au, Pd, Fe, etc. Preferred alloys include Ni—Co, Ni—Fe, Co—Fe, etc. In view of their economical aspect, preferred are Ni, Cr and Zn; and more preferred is Ni.

The thickness of the semi-transparent thin metal film is so controlled that the film does not prevent the intrinsic luster of metal. Specifically, the film must not completely hide the interference color of the metal oxide layer that covers the flaky pigment to present a dichroic interference color. The thin metal film that covers the substrate is semi-transparent, and this means that the film is thin, not presenting a metallic gloss of itself, and means that the masking ability of the film is not high. Accordingly, in the invention, thinner metal films are preferred as relaxing their dark shade peculiar to metal, and the pigment coated with such a thinner metal film presents a better color tone. The thin metal film enhance the reflectivity of metal oxide layers, so that, strong interference color is achieved, in addition, dichromatic effect is enhanced. Thus the thin metal film coating gives enhanced color effect to metal oxide coated metal flake, which originally has mono tone metallic color and weak interference color.

Preferably, in the invention, the thickness of the thin metal film to cover the metal oxide-coated flaky pigment substrate is at most 0.05 $\mu$m, more preferably from 0.01 to 0.04 $\mu$m.

Method for Producing Semi-transparent Thin Metal Film

An ordinary chemical plating method is preferred for forming the film. For this, used is a plating bath that contains a metal salt, a reducing agent, a complexing agent, a stabilizer, etc. The reducing agent includes, for example, sodium hypophosphite, sodium borohydride, formalin, hydrazine, etc.

The complexing agent includes, for example, formic acid, acetic acid, succinic acid, citric acid, tartaric acid, malic acid, glycine, ethylenediamine, EDTA, triethanolamine, etc.

Before being chemically plated, the flaky pigment is preferably pre-treated with, for example, an aqueous solution containing palladium chloride and hydrochloric acid for activating its surface.

The metal salt is a source of the plating metal, and it may be any and every soluble salt. For example, it includes Ni, Cu or Ag sulfates, hydrochlorides, nitrates, carbonates, etc.

Recently, a chemical plating method not requiring pretreatment for activation has been disclosed (Shikizai Kvokai-shi ("Journal of the Japan Society of Color Material"), 69 (6), 370–377 (1996)). In this, an acetylacetonato-metal complex is reduced in an organic solvent to thereby plate a substrate with the metal derived from the complex. When the plating bath is refluxed under heat with stirring, fine metal particles are formed therein and they uniformly deposit on the surfaces of fine inorganic particles of a substrate to thereby form a metal film to cover each substrate particle.

Not requiring pretreatment for activation, the method is simple and easy as compared with ordinary plating methods. Another advantage of the method is that the film formed in the method gives a continuous film consisting of much finer particles, rather than an intermittent film consisting of granule particles. Therefore, the reflection from the metal is reduced and the thin film has a uniform thickness.

For example, in the case of forming a nickel film on the surface (a metal oxide-coated flaky pigment substrate having interference color) according to this plating method, using bis(acetylacetonato)nickel(II) and hydrazine as a reducing agent in a polar aprotic solvent, dimethylsulfoxide (DMSO), a dense nickel film may be formed on the substrate.

However, if water, ethanol or the like is used as the solvent in this plating method, the intended, dense metal film could not be formed on the substrate.

The coating method does not include a step of cutting pigments, and therefore, even the edges of the metal oxide-coated flaky pigment substrate are uniformly coated with the thin metal film formed thereon, or that is, the pigment is entirely coated with the thin metal film formed to cover it.

Use

The high-chromatic flaky pigment coated with a thin metal film of the invention has many applications in various fields of, for example, paints, inks, printing inks, security inks, plastics, powder coatings, resin compositions, ceramics, earthenware, glazes, cosmetics, for the preparation of granules, etc. These are described in detail hereinunder.

Paints

Paints include, for example, organic solvent paints, NAD paints, aqueous paints, emulsion paints, colloidal paints, powdery paints.

In these paints, the amount of the pigment of the invention may fall between 1 and 100% by weight of the solid resin therein, preferably between 1 and 70% by weight, more preferably between 1 and 20% by weight thereof.

For improving its dispersibility in paints, the pigment of the invention may be processed with a silane coupling agent or a titanate coupling agent on its surface.

The resin component to be in the paints includes, for example, acrylic resin, alkyd resin, unsaturated polyester resin, amino resin, melamine resin, polyurethane resin, epoxy resin, polyamide resin, phenolic resin, cellulose resin, polyvinyl resin, silicone resin, fluororesin, etc. One or more such resins may be used either singly or as combined.

Containing a crosslinking resin such as acryl-melamine resin or the like, aqueous paints may form emulsion paints.

The constituents to form the paints are, for example, pigment, organic pigment, inorganic pigment, dyes, anti-sagging agent, viscosity-controlling agent, anti-settling agent, crosslinking promoter, curing agent, leveling agent, surface-controlling agent, defoaming agent, plasticizer, antiseptic agent, mildew-proofing agent, UV stabilizer, etc.

For example, the pigment includes titanium dioxide, calcium carbonate, clay, talc, barium sulfate, white carbon, chromium oxide, zinc oxide, zinc sulfide, zinc powder, metal powder pigments (e.g., aluminum flakes, colored aluminum flakes, stainless steel flakes, titanium flakes, etc.), iron black, yellow iron oxide, red iron oxide, chrome yellow, carbon black, molybdate orange, prussian blue, ultramarine, cadmium pigments, fluorescent pigments, soluble azo pigments, insoluble azo pigments, condensed azo pigments, phthalocyanine pigments, condensed polycyclic pigments, composite oxide pigments, graphite, mica (e.g., muscovite, phlogopite, synthetic mica, fluorotetra silicon mica, etc.), metal oxide-coated mica (e.g., titanium dioxide-coated mica, iron oxide (hydrate)-coated mica, iron oxide and titanium dioxide-coated mica, low-order titanium oxide-coated mica, etc.), metal oxide-coated graphite (e.g., titanium dioxide-coated graphite, etc.), flaky alumina, metal oxide-coated alumina (e.g., titanium dioxide-coated alumina, iron oxide-coated flaky alumina, diiron trioxide-coated flaky alumina, triiron tetroxide-coated flaky alumina, interferential metal oxide-coated flaky alumina, etc.), MIO, etc.

Combined with any of these pigments, the pigment of the invention may present a novel color tone and may have an additional function.

The paints may be applied to wood, plastics, steel sheets, glass, ceramics, paper, films, sheets and also to semitransparent films of reflectors for LC displays, etc.

Examples of the applications of the paints are automobiles, buildings, ships, electric and electronic appliances for household use, cans, industrial machines and instruments, road marking, plastics, household painting, etc.

Regarding its structure, the painted film may comprise, for example, an under-coat layer, an intermediate-coat layer, a layer containing the pigment of the invention, and a clear-coat layer that are layered in that order; or an under-coat layer, a layer containing the pigment of the invention, and a clear-coat layer layered in that order. For these, for example, employable is any coating mode of one coat-one bake; two coats-one bake; two coats-two bakes; three coats-one bake; three coats-two bakes; three coats-three bakes, etc. The coating process includes electrostatic coating, air spraying, airless coating, roll coating, dipping, etc.

Inks

The pigment of the invention is usable in various printing inks, such as letterpress printing inks, lithographic printing inks, intaglio printing inks, inks for metal plates, radiation-curable inks, UV inks, EB inks, flexographic printing inks, screen printing inks, off set printing inks gravure printing inks, security printing inks, etc.

In these inks, the amount of the pigment of the invention may fall between 1 and 100% by weight of the solid resin therein, preferably between 1 and 70% by weight, more preferably between 1 and 20% by weight thereof.

The pigment of the invention may be processed with a silane coupling agent or a titanate coupling agent on its surface.

The resin to be in the inks includes, for example, rosin-maleic resin, maleic resin, alkyd resin, polyamide resin, phenolic resin, petroleum resin, urethane resin, epoxy resin, acrylic resin, butyral resin, melamine resin, polyvinyl chloride, polyvinylidene chloride, cellulose resin, polyvinyl resin, unsaturated polyester resin, etc. One or more such resins may be used either singly or as combined.

The constituents to form the inks are, for example, pigment, organic pigment, inorganic pigment, and, as auxiliary agents, varnish, reducer, compound, extra-varnish, gelling agent, drying promoter, antioxidant, anti-setoff agent, lubricant, activator, etc. In addition, the inks may contain any of anti-sagging agent, viscosity-controlling agent, anti-settling agent, crosslinking promoter, curing agent, leveling agent, surface-controlling agent, defoaming agent, plasticizer, antiseptic agent, mildew-proofing agent, UV stabilizer, etc.

For example, the pigment includes extender pigments, precipitated bariumsulfate precipitated calcium carbonate, alumina white, magnesium carbonate, white carbon; white pigments such as titanium dioxide, zinc flower, etc.; black pigments such as carbon black; yellow pigments such as chrome yellow, disazo yellow, Hansa Yellow; red pigments such as Brilliant Carmine 6B, Lake Red C, Permanent Red F5R, rhodamine lake, etc.; blue pigments such as phthalocyanine blue, Victoria blue lake, prussian blue, etc.; orange pigments such as chrome bar million, disazo orange; green pigments such as phthalocyanine green, etc.; violet pigments such as methyl violet lake, dioxazine violet, etc.; and other pigments such as isoindolinone pigments, benzimidazoline pigments, condensed azo pigments, quinacridone pigments, etc.; as well as composite oxide pigments, graphite, mica (e.g., muscovite, phlogopite, synthetic mica, fluorotetra silicon mica, etc.), metal oxide-coated mica (e.g., titanium dioxide-coated mica, iron oxide (hydrate)-coated mica, iron oxide and titanium oxide-coated mica, low-order titanium oxide-coated mica, etc.), metal oxide-coated graphite (e.g., titanium dioxide-coated graphite, etc.), flaky alumina, metal oxide-coated alumina (e.g., titanium dioxide-coated alumina, iron oxide-coated flaky alumina, diiron trioxide-coated flaky alumina, triiron tetroxide-coated flaky alumina, interferential metal oxide-coated flaky alumina, etc.), MIO, etc.

The inks may be applied for example, to wood, plastics, steel sheets, glass, ceramics, paper, corrugated cardboard, films, sheets, cans and also to semitransparent films of reflectors for LC displays, etc.

Combined with any of these pigments, the pigment of the invention may present a novel color tone and may have an additional function. In prints, the optical effect of the interference pigment of the invention cannot be copied. Therefore, the printing ink that contains the pigment of the invention is effective for preventing forgeries of certificate matters such as checks, credit cards, gift certificates, securities, tickets, travel tickets, airline tickets, train tickets, identification cards, etc., for which the usefulness of the pigment of the invention is increasing.

Resin Composition

The pigment of the invention may be used in various resin compositions.

For improving its dispersibility in resin compositions, the pigment of the invention may be processed with a silane coupling agent or a titanate coupling agent.

In resin compositions, the amount of the pigment of the invention may fall between 0.1 and 50% by weight, preferably between 0.1 and 20% by weight, more preferably between 0.1 and 5% by weight.

For the resin compositions, usable are thermoplastic resin and thermosetting resin.

For example, they include polyethylene, chloropolyethylene, polypropylene, polymethylpentene, AAS, ABS, ACS, AES, AS, EEA, ethylene-vinyl acetate copolymer, EVOH, ionomers, methacrylic resin, PCT, polystyrene, polyvinyl chloride, polyvinylidene chloride, thermoplastic elastomers, thermoplastic polyurethane elastomers, diallyl phthalate resin, epoxy resin, melamine resin, phenolic resin, urea resin, polyesters, polyurethanes, silicone resin, polyamides, polybutylene terephthalate, polyethylene terephthalate, polyoxymethylene, polycarbonates, polyphenylene ether, unsaturated polyesters, fluororesin, polyether-ether ketones, polyether ketones, liquid crystal polymers, polyphenylene sulfide, polyarylates, polyaryl sulfones, polyether imides, polyether sulfones, polysulfones, polyamidimides, cellulose acetate, polybutadiene, polydicyclopentadiene, polyketones, polyphthalamide, EMAA, polybutene, polyacrylonitriles, polyacetals, polyvinyl acetals, amino resin, alkyd resin, biodegradable plastics (e.g., microbiological products such as bacteria cellulose, biopolyesters; chemical synthetic products such as polycaprolactam, polyethylene succinate, polylactic acid; natural substances such as starch, cellulose acetate, etc.), and their copolymers, block copolymers graft copolymers, as well as natural rubber, synthetic rubber, silicone rubber, etc.

The additives to the resin compositions may be pigment, dye, paint, crosslinking agent, vulcanizing agent, vulcanization promoter, antioxidant, anti-aging agent, plasticizer, UV absorbent, light stabilizer, filler, reinforcing agent, lubricant, flame retardant, antistatic agent, foaming agent, curing agent, modifying agent, etc.

For example, the pigment includes titanium dioxide, calcium carbonate, clay, talc, precipitated barium sulfate, white carbon, chromium oxide, zinc oxide, zinc sulfide, zinc powder, metal powder pigments, iron black, yellow iron oxide, red iron oxide, chrome yellow, carbon black, molybdate orange, prussian blue, ultramarine, cadmium pigments, fluorescent pigments, soluble azo pigments, insoluble azo pigments, condensed azo pigments, phthalocyanine pigments, condensed polycyclic pigments, composite oxide pigments, graphite, mica (e.g., muscovite, phlogopite, synthetic mica, fluorotetra silicon mica, etc.), metal oxide-coated mica (e.g., titanium dioxide-coated mica, iron oxide (hydrate) -coated mica, iron oxide and titanium oxide-coated mica, low-order titanium oxide-coated mica, etc.), metal oxide-coated graphite (e.g., titanium dioxide-coated graphite, etc.), flaky alumina, metal oxide-coated alumina (e.g., titanium dioxide-coated alumina, iron oxide-coated flaky alumina, diiron trioxide-coated flaky alumina, triiron tetroxide-coated flaky alumina, inter-ferential metal oxide-coated flaky alumina, etc.), MIO, etc.

Combined with any of these pigments, the pigment of the invention may present a novel color tone and may have an additional function.

The resin composition may be formed into, for example, resin moldings, laminates, films (for agriculture, food industry, constructional decoration industry, etc.), sheets (for agriculture, food industry, constructional decoration industry, etc.), wrapping and packaging materials, sheets or films for wrapping and packaging edibles and drinks, various containers, electric and electronic parts, electric and electronic appliances for household use, parts of OA and AV appliances, rubber products, automobile parts, finishing materials, decorativeplates, waved plates, building materials, wall boards, floor materials, wall paneling materials, bands, tires, caps, etc.

The resin compositions may be laser-masked, if desired.

For shaping and working the resin compositions, for example, employable are various methods of injection molding, casting, extrusion, transfer molding, inflation molding, stretching, vacuum forming, blow molding, calendering, lining, lamination, slushing, pasting, etc.

Cosmetics

Cosmetics include make-up cosmetics, hair cosmetics, etc. For example, they are gel, lipstick, foundation (emulsion-type, liquid-type, oil-type, etc.), rouge, mascara, nail enamel, eyebrow pencils, eye shadow, eye liner, hair color, etc., in any of which the pigment of the invention may be used.

In these, the amount of the pigment of the invention may fall between 1 and 100% by weight. For example, it may fall between 1 and 50% by weight in foundation; between 1 and 80% by weight in shadow; between 1 and 40% by weight in lipstick; and between 0.1 and 20% by weight in nail enamel.

The constituents to form the cosmetics are mentioned below.

Inorganic pigments and extender pigments are, for example, titanium dioxide, calcium carbonate, clay, talc, barium sulfate, white carbon, chromium oxide, zinc oxide, zinc sulfide, zinc powder, metal powder pigments, iron black, yellow iron oxide, red iron oxide, chrome yellow, carbon black, molybdate orange, prussian blue, ultramarine, cadmium pigments, fluorescent pigments, soluble azo pigments, insoluble azo pigments, condensed azo pigments, phthalocyanine pigments, condensed polycyclic pigments, composite oxide pigments, graphite, mica (e.g., muscovite, phlogopite, synthetic mica, fluorotetra silicon mica, etc.), metaloxide-coated mica (e.g., titanium dioxide-coated mica, iron oxide ($Fe_2O_3$ and/or $Fe_3O_4$) (hydrate)-coated mica, iron oxide ($Fe_2O_3$,$Fe_3O_4$) and titanium oxide-coated mica, low-order titanium oxide-coated mica, etc.), metal oxide-coated graphite (e.g., titanium dioxide-coated graphite, etc.), flaky alumina, metal oxide-coated alumina (e.g., titanium dioxide-coated alumina, iron oxide-coated flaky alumina, diiron trioxide-coated flaky alumina, triiron tetroxide-coated flaky alumina, interferential metal oxide-coated flaky alumina, etc.), MIO, sericite, magnesium carbonate, silica, zeolite, hydroxyapatite, cobalt titanate, glass beads, nylon beads, silicone beads, etc.

Organic pigments are, for example, Red 2, 3, 102, 104, 105, 106, 201, 202, 203, 204, 205, 206, 207, 208, 213, 214, 215, 218, 219, 220, 221, 223, 225, 226, 227, 228, 230-(1), 230-(2) 231, 232, and 405; Yellow 4, 5, 201, 202-(1), 202-(2), 203, 204, 205, 401, 402, 403, 404, 405, 406, and 407; Green 3, 201, 202, 204, 205, 401, and 402; Blue 1, 2, 201, 202, 203, 204, 205, 403, and 404; Orange 201, 203, 204, 205, 206, 207, 401, 402, and 403; Brown 201; Violet 201, and 401; Black 401, etc.

Natural colors are, for example, salol yellow, carthamin, β-carotene, hibiscus colors, capsanthin, carminic acid, laccaic acid, curcumin, riboflavin, shikonin, etc.

The cosmetics may further contain any of oil, fat, wax, surfactant, antioxidant, UV absorbent, vitamins, hormones, squalane, liquid paraffin, palmitic acid, stearic acid, bees wax, myristyl myristate and other hydrocarbons; organic solvents such as acetone, toluene, butyl acetate and other acetates; and also, antiseptic agent, polyalcohols, fragrances, etc.

Combined with any of the pigments mentioned above, the pigment of the invention may present a novel color tone and may have an additional function.

Others

Apart from the above, the pigment of the invention may also be incorporated into color toners for duplicators, ceramics, earthenware, porcelain, glazes, etc.

For example, it is incorporated into glass, new ceramics, fine ceramics, refractory materials, cement, etc. In particular, when it is used in color toners for duplicators, it acts to prevent forgeries as in the above, owing to its flip-flop, i.e., color flop effect, property.

The entire disclosure [s] of all applications, patents and publications, cited above or below, and of corresponding Japanese Application No. 01-282600, filed Sep. 18, 2001, is hereby incorporated by reference.

EXAMPLES

In the foregoing and in the following examples, all temperatures are set forth uncorrected in degrees Celsius; and, unless otherwise indicated, all parts and percentages are by weight.

The high-chromatic flaky pigment of the invention is described in more detail with reference to the following Examples and Comparative Examples, which, however, are not intended to restrict the scope of the invention.

Example 1

$Ni/TiO_2/SiO_2$/Aluminum Flakes (1) Coating with 3.6% $SiO_2$

Aluminium flakes (50 g) (Toyo Aluminum's Aluminum PASTE 1810YL with BET surface area of 2.07 $m^2/g$ and D50 of 20 μm) were washed with acetone, and filtered. To the filtered cake, were added ethanol (340 g) and tetraethoxysilane (TEOS) (5 g). A liquid mixture of water (10 g) and a silane coupling agent, SH6020 (2 g) was added to the resulting suspension of aluminum flakes. The suspension was stirred at room temperature for 20 hours, then filtered and dried.

(2) Coating with 55.4% $TiO_2$

The $SiO_2$-coated aluminum flakes (10 g) were suspended in a liquid mixture of tetraethoxy-orthotitanate (40.6 g) and ethanol (250 g). A liquid mixture of water (40 g) and ethanol (360 g) was gradually added (1 ml/min) to the resulting suspension with stirring. This was stirred at room temperature for 14 hours. Next, the suspension was heated (50° C.), and water (200 g) was gradually added (1 ml/min) thereto with stirring. After stirred (50° C., 5 hours), this was filtered and dried to obtain a powder (its BET surface area was about 200 $m^2$/g.). This powder presented a green interference color. However, on a white/black hiding power test sheet, the interference color of this powder was weak. The color of the pigment was measured. Concretely, the pigment was mixed with a VS medium and spread on a substrate, and its color was measured. For the measurement, used was a calorimeter, Minolta Camera's CR300. The data are shown in Table 1.

(3) Coating with 5.7% Ni

Bis (acetylacetonato) nickel dihydrate (Ni $(C_5H_7O_2)_2 \cdot 2H_2O$ (0.3 g)) and $(NH_2)_2 \cdot H_2O$ (1.5 g) were added to dimethylsulfoxide (DMSO) (150 g), and the $TiO_2$-coated aluminum flakes (1g) was suspended in the resulting solution. The suspension was refluxed with stirring (120° C., 15 minutes). The product was filtered, washed with acetone, and dried to obtain a powder. Based on the data obtained through actual measurement, the thickness of the Ni film formed around each particle of the powder was calculated, and was 0.034 $\mu$m.

On a white/black hiding power test sheet, the powder presented a deep green interference color within a broad angle. As coated with Ni, the interference color of the pigment was enhanced, and its saturation was high. At different viewing angles, the pigment presented a good flip-flop appearance, varying yellowish green to bluish green.

The color of the pigment was measured. Concretely, the pigment was mixed with a medium and spread on a white sheet, and its color was measured. The data are given in Table 1. For the measurement, used was a calorimeter, Minolta Camera's CR300.

The data confirm that the bluish green color of the pigment coated with a thin Ni film presents was enhanced and the saturation thereof was increased.

TABLE 1

| Color | value a | value b | value c |
| --- | --- | --- | --- |
| Before coated with Ni (2) | −3.38 | +3.14 | 4.61 |
| After coated with Ni (3) | −8.04 | +12.30 | 14.69 |

Comparative Example 1

In the Ni-coating step in Example 1, ethanol and not DMSO was used. The powdery pigment produced was coated with Ni. However, the Ni film formed was not dense but was somewhat porous.

Comparative Example 2

After coated with $TiO_2$ in Example 1, the pigment was baked (350° C., 1 hour). This was coated with Ni in the same manner, but it could not present a strong interference color. Probably, as baked, the $TiO_2$ layer lost its activity.

Production Example 1

| Paint Compositions Pearl base paint: | |
| --- | --- |
| Composition A | |
| Acrydic 47-712 | 70 wt. pts. |
| Superbeccamine | 30 wt. pts. |
| Composition B | |
| Pigment of Example 1 | 10 wt. pts. |
| Pearl pigment | 10 wt. pts. |
| Composition C | |
| Ethyl acetate | 50 wt. pts. |
| Toluene | 30 wt. pts. |
| N-butanol | 10 wt. pts. |
| Solvesso #150 | 40 wt. pts. |

100 parts by weight of the composition A and 20 parts by weight of the composition B were mixed, and diluted with the composition C to have a viscosity suitable for spraying (12 to 15 seconds measured with Ford Cup #4). This was sprayed on substrate to form a base coat layer thereon.

| Clear coat paint: | |
| --- | --- |
| Acrydic 44-179 | 14 wt. pts. |
| Superbeccamine | 6 wt. pts. |
| Toluene | 4 wt. pts. |
| MIBK | 4 wt. pts. |
| Butyl cellosolve | 3 wt. pts. |

This composition was coated over the base coat, dried in air at 40° C. for 30 minutes and then baked (130° C., 30 minutes)

Production Example 2

| Plastic | |
| --- | --- |
| High-density polyethylene (pellets) | 100 wt. pts. |
| Pigment of Example 1 | 1 wt. pt. |
| Magnesium stearate | 0.1 wt. pts. |
| Zinc stearate | 0.1 wt. pts. |

These were dry-blended, and injection-molded.

Production Example 3

| Ink | |
| --- | --- |
| CCST medium (nitrocellulose resin) | 10 wt. pts. |
| Pigment of Example 1 | 8 wt. pts. |

The composition of the two was diluted with a solvent NC102 to have a viscosity of 20 seconds (measured with Zatin Cup No. 3). This is a printing ink.

Production Example 4

| Compact powder | |
|---|---|
| Talc | 50 wt. pts. |
| Pigment of Example 1 | 25 wt. pts. |
| Color pigment | 5 wt. pts. |
| Isopropyl myristate | ad lib. |
| Magnesium stearate | 2 wt. pts. |
| Foundation | |
| Talc | 38 wt. pts. |
| Pigment of Example 1 | 25 wt. pts. |
| Mica (8 μm) | 10 wt. pts. |
| Magnesium stearate | 3 wt. pts. |
| Nylon powder 12 | 8 wt. pts. |
| Yellow iron oxide | 1.9 wt. pts. |
| Red iron oxide | 0.8 wt. pts. |
| Titanium dioxide | 1.0 wt. pts. |
| Mineral oil | ad lib. |
| (Caprylic acid, capric acid) triglyceride | 3.3 wt. pts. |
| Butylparaben | 0.1 wt. pts. |

According to the invention, a flaky pigment having a interference color by itself is further coated with a semi-transparent thin metal film to produce a high-chromatic flaky pigment having a dichromatic color effect. According to the method of the invention, the high-chromatic flaky pigment can be produced in a simple and inexpensive plant, not requiring a large-scale apparatus.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A high-chromatic flaky pigment which comprises a flaky substrate of a metal flake pigment coated with a silicon dioxide film or an aluminum oxide film or a silica and alumina film, as a protective film, the substrate being coated over its entire surface with a metal oxide, selected from a group consisting of titanium dioxide, zirconium oxide, iron oxide, tin oxide, zinc oxide and cerium oxide, providing an interference color and further coated with a semi-transparent thin metal film to enhance the interference color of the pigment, wherein the pigment exhibits a color flop effect.

2. The high-chromatic flaky pigment as claimed in claim 1, wherein the semi-transparent thin metal film has a thickness of less than 0.05 μm.

3. The high-chromatic flaky pigment as claimed in claim 1, wherein the semi-transparent thin metal film is formed of one or more metals selected from the group consisting of Ni, Zn, Cr, Co, Cu, Pt, Ag, Au, and alloys thereof.

4. The high-chromatic flaky pigment as claimed in claim 2, wherein the semi-transparent thin metal film is formed of one or more metals selected from the group consisting of Ni, Zn, Cr, Co, Cu, Pt, Ag, Au, and alloys thereof.

5. The high-chromatic flaky pigment as claimed in claim 1, wherein the semi-transparent thin metal film is a dense film of metal particles continuously well ordered therein.

6. The high-chromatic flaky pigment as claimed in claim 1, wherein the semi-transparent thin metal film is formed through reduction of an acetylacetonato-metal complex in an organic solvent.

7. The high-chromatic flaky pigment as claimed in claim 5, wherein the semi-transparent thin metal film is formed through reduction of an acetylacetonato-metal complex in an organic solvent.

8. The high-chromatic flaky pigment as claimed in claim 1, wherein the flaky substrate is aluminum flake coated with a silicon dioxide film or an aluminum oxide film or a silica and alumina film, as a protective film.

9. A method for producing a high-chromatic flaky pigment, which pigment comprises a flaky substrate of a metal flake pigment, the substrate being coated over its entire surface with a metal oxide providing an interference color and further coated with a semi-transparent thin metal film to enhance the interference color of the pigment, wherein the process comprises coating the entire surface of the flaky substrate with a metal oxide, further coating the entire surface of the metal oxide-coated flaky pigment with a metal layer through reduction of an acetylacetonato-metal complex in an organic solvent, and drying it to form a semi-transparent thin metal film thereon.

10. A paint, ink, printing ink, security ink, powder coating, plastic, resin molding, cosmetic, or security document which comprises the high-chromatic flaky pigment of claim 1.

11. A method for producing a high-chromatic flaky pigment of claim 1, which comprises coating the entire surface of the flaky substrate with the metal oxide, further coating the entire surface of the metal oxide-coated flaky pigment with a metal layer through reduction of an acetylacetonato-metal complex in an organic solvent, and drying it to form a semi-transparent thin metal film thereon.

12. A high-chromatic flaky pigment of claim 1, wherein the semi-transparent thin metal film is provided over the entire surface of the metal oxide coating.

13. A high-chromatic flaky pigment of claim 1, wherein the flaky substrate is of particles with an average size falling between 5 and 100 μm and a thickness falling between 0.1 and 5 μm.

14. A high-chromatic flaky pigment of claim 1, wherein the amount of the protective film on the flaky substrate is between 0.1 and 10% by weight of the flaky substrate.

15. A high-chromatic flaky pigment of claim 1, wherein the metal oxide coating is of titanium dioxide.

16. A high-chromatic flaky pigment of claim 1, wherein the optical thickness of the metal oxide coating is between 90 and 360 nm.

17. A high-chromatic flaky pigment of claim 1, wherein the semi-transparent thin metal film is an alloy of Ni—Co, Ni—Fe, or Co—Fe.

18. A high-chromatic flaky pigment of claim 1, wherein the semi-transparent thin metal film is of Ni, Cr or Zn.

19. A high-chromatic flaky pigment of claim 1, wherein the semi-transparent thin metal film is of Ni.

20. A high-chromatic flaky pigment of claim 1, wherein the semi-transparent thin metal film has a thickness of at most 0.05 μm.

* * * * *